United States Patent [19]

Christy

[11] 3,950,423

[45] Apr. 13, 1976

[54] 10,11-DIHYDRO-10,10,11,11-TETRAFLUORO-5H-DIBENZO[A,D]CYCLOHEPTENE-5-METHYLAMINES

[75] Inventor: Marcia Elizabeth Christy, Perkasie, Pa.

[73] Assignee: Merck & Co., Inc., Rahway, N.J.

[22] Filed: Feb. 1, 1974

[21] Appl. No.: 438,924

[52] U.S. Cl. .......... 260/570.9; 260/349; 260/453 A; 260/471 C; 260/475 FR; 260/515 A; 260/516; 260/501.1; 260/556 AR; 260/570.8 TC; 260/607 B; 260/609 R; 260/612 R; 260/618 F; 260/649 F; 260/520 B; 260/590 FB; 424/316; 424/330

[51] Int. Cl.² ........................................ C07C 87/29

[58] Field of Search ................ 260/570.9, 501.1

[56] References Cited

UNITED STATES PATENTS 3,707,562   12/1972   Schindler et al. ............ 260/570.9 X Primary Examiner—Robert V. Hines
Attorney, Agent, or Firm—Daniel T. Szura; J. Jerome Behan

[57] ABSTRACT

Tetrafluoro derivatives of 10,11-dihydrodibenzo[a,d]cyclohepten-5-aminomethyl compounds and the corresponding N-substituted derivatives thereof, useful as antiarrhythmic agents, are prepared from tetrafluoro derivatives of 10,11-dihydro-5H-dibenzo[a,d]cyclohepten-5-one by reduction to the corresponding 5-ol compound and subsequently converting said 5-ol compound to the corresponding 5-halo and the 5-aminomethyl derivatives by reactions known in the prior art.

7 Claims, No Drawings

10,11-DIHYDRO-10,10,11,11-TETRAFLUORO-5H-DIBENZO[A,D]CYCLOHEPTENE-5-METHYLAMINES

This invention relates to tetrafluoro derivatives of 10,11-dihydro-dibenzo[a,d]cyclohepten-5-aminomethyl compounds and the corresponding N-substituted derivatives, such as the N-alkyl and N,N-dialkyl derivatives thereof. More specifically, it relates to substituted and unsubstituted derivatives of 10,11-dihydro-10,10,11,11-tetrafluoro-5H-dibenzo[a,d]cycloheptene-5-methylamine and to the N-alkyl, e.g., N-methyl or N-ethyl, and the N,N-dialkyl, e.g., N,N-dimethyl or N,N-diethyl derivatives thereof.

This invention also relates to the novel processes and the novel intermediates utilized in the production of the new 10,10,11,11-tetrafluoro-5H-dibenzo[a,d]cycloheptene-5-methylamines, to pharmaceutical formulations of the new tetrafluorodibenzocycloheptene methylamines, and to methods of treating or preventing cardiac arrhythmias using the novel compounds and/or pharmaceutical formulations thereof described hereinafter.

The new compounds of this invention are 10,11-dihydro-10,10,11,11-tetrafluoro-5H-dibenzo[a,d]cycloheptene-5-methylamines and the corresponding N-substituted and N-alkyl or N,N-dialkyl derivatives thereof represented by the following forula:

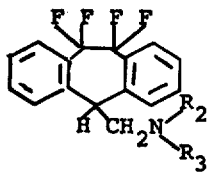

wherein
$R_2$ and $R_3$ can be alike or different and are either hydrogen, alkyl, aralkyl, alkenyl, alkynyl, or can be joined together through an atom of nitrogen, oxygen, or sulfur to form a heterocyclic ring of from 5–6 atoms, or a derivative of one of the above tetrafluorodibenzocycloheptene-methylamine compounds in which one or more of the hydrogen atoms attached to the 1-, 2-, 3-, 4-, 6-, 7-, 8- or 9- positions is replaced by halogen, alkyl, alkoxy, perfluoroalkyl, alkylmercapto, alkylsulfonyl, and dialkylsulfamoyl.

A preferred class of compounds of the present invention may be represented structurally in accordance with the above formula in which the $R_2$ and $R_3$ substituents are preferably loweralkyl substituents of from 1–6 carbon atoms or hydrogen, and the ring substituent at the 1-, 2-, 3-, 4-, 6-, 7-, 8- or 9- position is either hydrogen, halogen selected from chlorine or fluorine, loweralkyl of from 1–6 carbon atoms, loweralkoxy of from 1–5 carbon atoms, trifluoromethyl, loweralkyl mercapto of from 1–6 carbon atoms, loweralkyl sulfonyl of from 1–6 carbon atoms, and dialkylsulfamoyl of from 2–8 carbon atoms.

An especially preferred group of compounds included within the scope of the present invention is represented by the formula

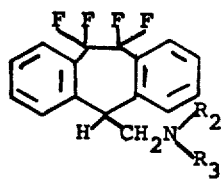

in which the $R_2$ and $R_3$ substituents are either hydrogen, loweralkyl of from 1–6 carbon atoms or any combination thereof. Illustrative of the compounds included within the scope of the present invention are 10,11-dihydro-10,10,11,11-tetrafluoro-5H-dibenzo[a,d]cycloheptene-5-methylamine, the N-methyl derivative of 10,11-dihydro-10,10,11,11-tetrafluoro-5H-dibenzo[a,d]cycloheptene-5-methylamine, and the N,N-dimethyl derivative of 10,11-dihydro-10,10,11,11-tetrafluoro-5H-dibenzo[a,d]cycloheptene-5methylamine.

Also included among the compounds useful in the method of the present invention are the N-oxides of the tertiary amines and the non-toxic pharmaceutically acceptable salts of the amines and N-oxides, the preferred salts being the non-toxic acid addition salts such as the hydrochloride, the maleate, and the like.

The compounds represented above, in either their free base or salt form, possess useful pharmacological properties. In particular, they have been found to possess antiarrhythmic activity. It has been found that the administration of compounds of the present invention, depicted in the above formula, results in the prevention of arrhythmia in animals under conditions which ordinarily cause the development of arrhythmia in the animal 100 percent of the time.

It has further been found that administration of the compounds of the present invention will arrest an existing arrhythmia in the animal being treated and cause a resumption of normal cardiac rhythm. As antiarrhythmic agents, these compounds may be administered orally or parenterally. The formulations for administration may be prepared in coventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, lactic acid, gluconic acid, maleic acid, succinic acid, tartaric acid, and the like. Salts of these acids with the amine base are useful as the active component of the composition in the method of this invention.

The daily doses are based on the total body weight of the test animal and vary between about 1.00 and 100.00 mg./kg. for mature animals. Thus, a unit dose based on four-times-a-day administration is between 2.5 mg. and 250 mg. for a 10 kg. dog, and a total daily dose for a 10 kg. dog would vary between about 10 mg. and 1000 mg. For larger animals, up to 100 kg. and above, proportional dosages are employed, based on the weight of the animal. Suitable dosage units provided for the administration of of the compositions used in the method of the invention are tablets, capsules (which may be suitably formulated for either immediate or sustained release), syrups, elixirs, parenteral solutions, and the like. These dosage forms preferably contain per unit one or more multiples of the desired dosage unit in combination with the pharmaceutically acceptable diluent or carrier required for preparing the dosage unit.

The condition of arrhythmia is a change in the normal rhythm of the heart which is noted in the higher forms of life, particularly the larger mammals including dogs, horses, cattle and man. This disturbance in the normal rhythm of the heart of the affected animal may arise spontaneously without apparent cause or it may result from a serious heart condition. Depending on the type of arrhythmia present in the affected patient, it may vary from a momentary effect which will spontaneously be corrected, or in extremely acute cases may result in almost instantaneous death. It is therefore desirable to provide a method of treatment for acute episodes of arrhythmia in the affected patient or, alternatively, to provide a method or prophylaxis including the administration of an agent useful in preventing arrhythmias to patients prone to such disturbances or normal heart rhythm.

One of the principal methods of treating arrhythmia using drug therapy in the past has been the administration of quinidine or procaine amide. This method suffers from toxic side effects associated with the drugs which often occur concurrently with the administration of the drug. Particularly important are gastrointestinal disturbances caused by the drugs as well as the possibility of vascular collapse. One difficulty with the administration of these prior art drugs is that the toxic side effects occur at a dosage level recommended for effective control of the arrhythmia.

In addition to quinidine and procaine amide, which have been the drugs of choice for treating arrhythmia in the past, other compounds more closely related in structure to the compounds of the present invention have been reported to be active as antiarrhythmic agents. Thus, U.S. Pat. No. 3,527,871 of Engelhardt and Torchiana reports that certain dibenzocycloheptene-5-methylamines are active as antiarrhythmic agents. However, it has been noted in the past that certai pharmacologically active dibenzocycloheptene compounds are metabolized through oxidation of the cycloheptene ring structure at the 10 or 11 carbons, i.e., the ethane or ethylene bridge between th two rings. In accordance with the present invention, there is produced a class of 10,10,11,11-tetrafluoro-10,11-dihydro-5H-dibenzo[a,d]cycloheptenes which have a perfluorinated ethane substituent bridging the benzene rings. This perfluoro ethane bridge is resistant to known chemical means of oxidation. The class of compounds however has been found to be active as antiarrhythmic agents, as shown by the ability of the compounds to arrest an existing arrhythmia or prevent the development of arrhythmia in animals under conditions which ordinarily cause such disturbances of the heart rhythm.

It has now been found in accordance with the present invention that administration of the compounds of the present invention depicted in the above formula results in the prevention of arrhythmia in animals under conditions which ordinarily cause the development of arrhythmia in the animal 100 percent of the time. It has further been found that administration of the compounds of the present invention will arrest an existing arrhythmia in the animal being treated and cause a resumption of normal cardiac rhythm.

The compounds represented by the above structural formulae may be prepared as illustrated below:

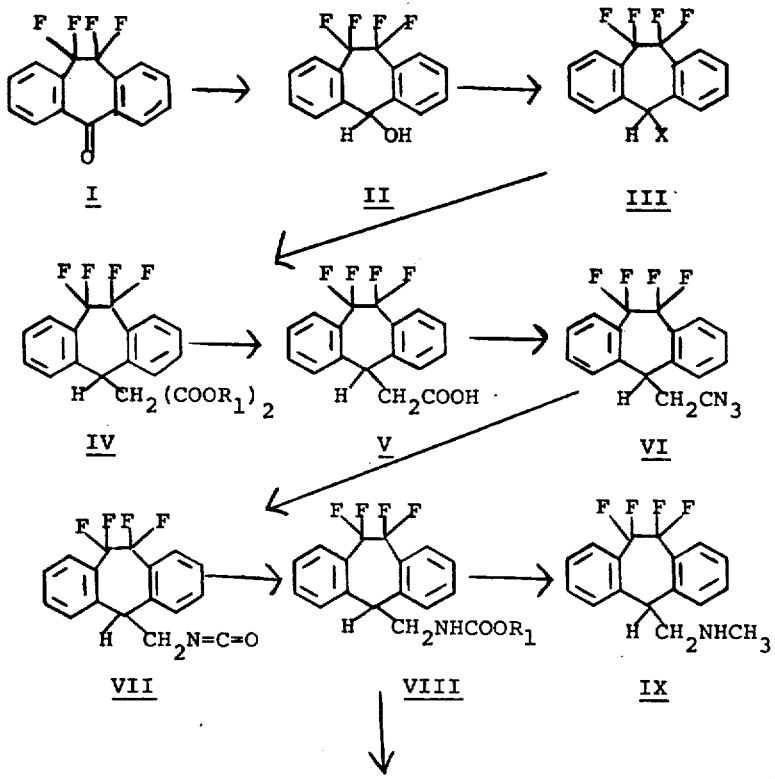

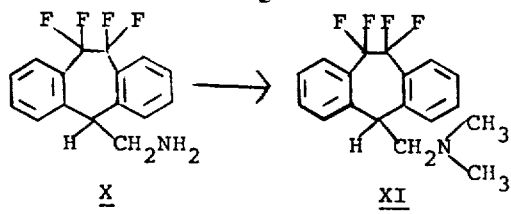

in which $R_1$ is a loweralkyl substituent and X is halogen. As indicated hereinabove, the aromatic rings of the above compounds are substituted optionally by replacement by one or more of the hydrogen atoms attached to the 1-, 2-, 3-, 4-, 6-, 7-, 8-, or 9- positions by halogen, especially chlorine or bromine, alkyl, preferably of from 1–6 carbon atoms, alkoxy, preferably loweralkoxy of from 1–5 carbon atoms, perfluoroalkyl, especially trifluoromethyl or pentafluoroethyl, alkylmercapto, preferably containing from 1–6 carbon atoms, alkylsulfonyl, preferably of from 1–6 carbon atoms, and dialkylsulfamoyl, preferably having from 2–8 carbon atoms.

In carrying out the process of the present invention, Compound I herein above, 10,11-dihydro-10,10,11,11-tetrafluoro-5H-dibenzo[a,d]cyclohepten-5-one, or a derivative thereof, is contacted with a reducing agent selected from alkali or alkaline earth metal borohydrides, dissolved in a solvent relatively inert under reaction conditions comprising either a loweralkanol such as ethyl alcohol or isopropyl alcohol or an ether, such as dioxane or tetrahydrofuran, at a temperature of from 0°C. to the reflux temperature of the solvent for a period of from 1–6 hours to produce a corresponding 10,11-dihydro-10,10,11,11-tetrafluoro-5H-dibenzo[a,d]cyclohepten-5-ol which, in turn, is treated with a halide compound selected from hydrogen chloride or hydrogen bromide, a phosphorous halide such as phosphorous pentachloride, or thionyl chloride. In carrying out the steps of the reaction, the cyclohepten-5-ol compound is treated with stirring at a temperature between about 0°–50°C. with thionyl chloride in at least equimolar amounts to produce the corresponding 5-chloro-10,11-dihydro-10,10,11,11-tetrafluoro-5H-dibenzo[a,d]cycloheptene. The chloro substituent of the dibenzocycloheptene compound is then replaced with a malonic ester substituent by contacting the 5-halo compound with a loweralkyl ester of malonic acid in the presence of a strong base such as sodium hydride at a temperature of from 0°C. to 100°C. Preferably the malonate ester is first mixed with sodium hydride in mineral oil and the solution of malonic ester is then treated with an appropriate amount of the 5-chloro-10,11-dihydro-10,10,11,11-tetrafluoro-5H-dibenzo[a,d]cycloheptene to produce the desired 10,11-dihydro-10,10,11,11-tetrafluoro-5H-dibenzo[a,d]-cycloheptene-5-malonate dialkyl ester. The malonate ester is then decarboxylated by heating with a solution of a strong base, advantageously an alcoholic solution of an alkali metal hydroxide, to produce a corresponding 10,11-dihydro-10,10,11,11-tetrafluoro-5H-dibenzo[a,d]-cycloheptene-5-acetic acid.

The acetic acid derivative is then rearranged utilizing known reaction conditions by first forming the corresponding acid azide, rearranging the azide to the isocyanate by heating, and treating a solution of the isocyanate with methanol to produce the N-methoxy carbonyl derivative of 10,11-dihydro-10,10,11,11-tetrafluoro-5H-dibenzo[a,d]cycloheptene-5-methylamine.

The N-methoxycarbonyl derivative thus formed is hydrolyzed to produce the corresponding primary amine, 10,11-dihydro-10,10,11,11-tetrafluoro-5H-dibenzo[a,d]cycloheptene-5-methylamine. The cycloheptene-5-methylamine compound is then converted by treatment with formaldehyde and formic acid in accordance with the known Eschweiler-Clarke modification of the Leuckart Reaction to produce the corresponding N,N-dimethyl derivative of 10,11-dihydro-10,10,11,11-tetrafluoro-5H-dibenzo[a,d]cycloheptene-5-methylamine.

In an alternative step of the process, the formed N-alkoxycarbonyl derivative of 10,11-dihydro-10,10,11,11-tetrafluoro-5H-dibenzo[a,d]cycloheptene-5-methylamine is reduced with an alkali metal aluminum hydride to produce the corresponding secondary amine, i.e., the N-methyl derivative of the preceding compound.

The starting material utilized in the process of the present invention is readily prepared from the known 10,11-dihydro-5H-dibenzo[a,d]cycloheptene-10,11-dione by reaction with sulfur tetrafluoride in the presence of hydrogen fluoride at a temperature of from 100°–160°C. for a period of several hours. In carrying out this conversion, it is preferable to first mix the reactants, i.e., the dione compound, along with the sulfur tetrafluoride and a small amount of hydrogen fluoride as a catalyst, and agitate for first 2 hours at 120°C. followed by elevation of the temperature for an additional 2 hours at 140°C., followed by elevation of the temperature for an additional 6 hours at 160°C. When the dione is treated in this manner, the desired 10,11-dihydro-10,10,11,11-tetrafluoro-5H-dibenzo[a,d]cyclohepten-5-one is obtained. The tetrafluoroketone prepared in this manner is then purified using a combination of techniques involving sublimation, column chromatography, and recrystallization. In order to prepare derivatives of the 10,11-dihydro-5H-dibenzo[a,d]cycloheptene-10,11-dione in which one of the hydrogens at the 1-, 2-, 3-, 4-, 6-, 7-, 8- or 9- positions is replaced by a substituent selected from halogen, alkyl, alkoxy, perfluoroalkyl, alkylmercapto, alkylsulfonyl, and dialkylsulfamoyl, it is preferred to employ an appropriately substituted o-benzyl benzoic acid. Available o-benzyl benzoic acids having the desired substitution in the aromatic rings are employed or known techniques for introducing the desired substituent in the desired position of the aromatic ring are employed. The benzyl benzoic acid is subjected to a homologation procedure involving reduction of the acid to the corresponding benzyl alcohol with lithium aluminum hydride, conversion of the benzyl alcohol to the corresponding benzyl bromide using hydrogen bromide, reaction of the benzyl bromide with an alkali metal cyanide to produce the corresponding o-benzyl phenylacetonitrile, followed by hydrolysis of the nitrile under acidic conditions to produce the corresponding o-benzyl phenylacetic acid compound. This phenyl acetic acid compound is then treated in a Friedel-Crafts type reaction using anhydrous aluminum chloride to produce the 10,11-dihydro-10-oxo-5H-dibenzo[a,d]cycloheptene, which in turn is oxidized using a mild oxidizing agent such as selenous acid, to produce the starting material utilized in the process of the present invention, i.e., the 10,11-dihydro-5H-dibenzo[a,d-]cycloheptene- 10,11-dione or a derivative thereof in which the ring substitutent at the 1-, 2-, 3-, 4-, 6-, 7-, 8- or 9-positions is either hydrogen, halogen selected from chlorine or fluorine, loweralkyl of from 1–6 carbon atoms, loweralkoxy of from 1–5 carbon atoms, trifluoromethyl, loweralkyl mercapto of from 1–6 carbon atoms, loweralkyl sulfonyl of from 1–6 carbon atoms, and dialkylsulfamoyl of from 2–8 carbon atoms. This method of preparing the starting material is outlined structurally below:

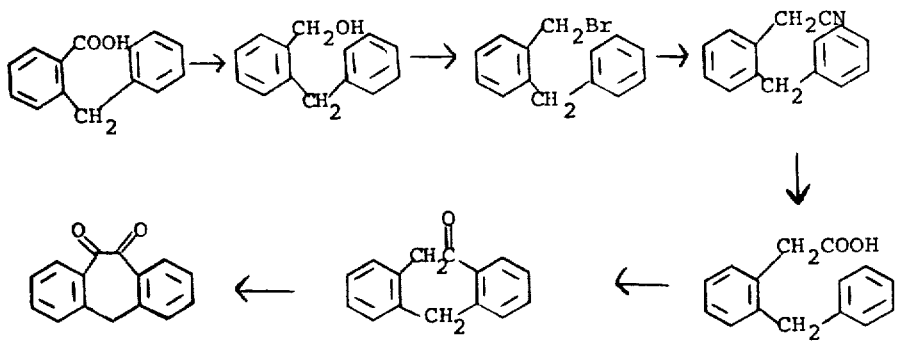

PREPARATION OF STARTING MATERIALS
PREPARATION 1.

- 10,11-Dihydro-10,10,11,11-tetrafluoro-5H-dibenzo[a,d]cyclohepten-5-one 10,11-Dihydro-5H-dibenzo[a,d]cyclohepten-10,11-dione, 0.8 g. (0.0036 mole), together with 75 g. of sulfur tetrafluoride, 1 g. of mercury and a trace of hydrogen fluoride, is charged into a stainless steel autoclave and shaken 2 hours at 120°C., 2 hours at 140°C. and 6 hours at 160°C. After cooling and venting the vessel, the mixture is dissolved in chloroform, separated from mercury, and filtered through diatomaceous earth. Evaporation of solvent from the filtrate under reduced pressure leaves an oily black solid as the residue that is triturated with 75 ml. of boiling hexane. The hexane-insoluble material is removed by filtration and evaporation of solvent from the filtrate under reduced pressure leaves the crude product as an oily black solid. Sublimation at 70°–75°C. and 0.05 mm. yields slightly oily, pale yellow crystals, m.p. 69°–77°C. to a cloudy melt clear at 110°C. Purification is effected by column chromatography on 50 g. of silica gel, the product being eluted with carbon tetrachloride. The fractions that show one spot of Rf 0.2 on a silica thin layer plate developed with carbon tetrachloride are combined. Evaporation of the solvent uner reduced pressure leaves white crystals, m.p. 73°–76°C. A sample for analysis is sublimed at 65°C. and 0.05 mm. and recrystallized twice from isopropyl alcohol-water; m.p. 75.5°–77.5°C.

Anal. Calc'd. for $C_{15}H_8F_4O$: C, 64.28; H, 2.88; F, 27.12. Found: C, 64.04; H, 2.88; F, 27.04.

The procedure of the preceding paragraph is repeated utilizing as the starting material the appropriate amount of the substituted 10,11-dihydro-5H-dibenzo[a,d]cyclohepten-10,11-dione to produce the correspondingly substituted 10,11-dihydro-10,10,11,11-tetrafluoro-5H-dibenzo[a,d]cyclohepten-5-one, as follows:

| STARTING MATERIAL | PRODUCT |
| --- | --- |
| 10,11-dihydro-1-fluoro-5H-dibenzo[a,d]cyclohepten-10,11-dione | 10,11-dihydro-1,10,10,11,11-pentafluoro-5H-dibenzo[a,d]cyclohepten-5-one |
| 3-chloro-10,11-dihydro-5H-dibenzo[a,d]cyclohepten-10,11-dione | 3-chloro-10,11-dihydro-10,10,11,11-tetrafluoro-5H-dibenzo[a,d]cyclohepten-5-one |
| 10,11-dihydro-3-methyl-5H-dibenzo[a,d]cyclohepten-10,11-dione | 10,11-dihydro-3-methyl-10,10,11,11-tetrafluoro-5H-dibenzo[a,d]cyclohepten-5-one |
| 3,7-dimethyl-10,11-dihydro-5H-dibenzo[a,d]cyclohepten-10,11-dione | 3,7-dimethyl-10,11-dihydro-10,10,11,11-tetrafluoro-5H-dibenzo[a,d]cyclohepten-5-one |
| 10,11-dihydro-4-methoxy-5H-dibenzo[a,d]cyclohepten-10,11-dione | 10,11-dihydro-4-methoxy-10,10,11,11-tetrafluoro-5H-dibenzo[a,d]cyclohepten-5-one |
| 10,11-dihydro-3-ethoxy-5H-dibenzo[a,d]cyclohepten-10,11-dione | 10,11-dihydro-3-ethoxy-10,10,11,11-tetrafluoro-5H-dibenzo[a,d]cyclohepten-5-one |
| 3,7-diethoxy-10,11-dihydro-5H-dibenzo[a,d]cyclohepten-10,11-dione | 3,7-diethoxy-10,11-dihydro-10,10,11,11-tetrafluoro-5H-dibenzo[a,d]cyclohepten-5-one |
| 10,11-dihydro-3-trifluoromethyl-5H-dibenzo[a,d]cyclohepten-10,11-dione | 10,11-dihydro-3-trifluoromethyl-10,10,11,11-tetrafluoro-5H-dibenzo[a,d]cyclohepten-5-one |
| 10,11-dihydro-3-methylmercapto-5H-dibenzo[a,d]cyclohepten-10,11-dione | 10,11-dihydro-3-methylmercapto-10,10,11,11-tetrafluoro-5H-dibenzo[a,d]cyclohepten-5-one |
| 10,11-dihydro-4-propylmercapto-5H-dibenzo[a,d]cyclohepten-10,11-dione | 10,11-dihydro-4-propylmercapto-10,10,11,11-tetrafluoro-5H-dibenzo[a,d]cyclohepten-5-one |
| 10,11-dihydro-3-ethylsulfonyl-5H-dibenzo[a,d]cyclohepten-10,11-dione | 10,11-dihydro-3-ethylsulfonyl-10,10,11,11-tetrafluoro-5H-dibenzo[a,d]cyclohepten-5-one |
| 3-diethylsulfamoyl-10,11-dihydro-5H-dibenzo[a,d]cyclohepten-10,11-dione | 3-diethylsulfamoyl-10,11-dihydro-10,10,11,11-tetrafluoro-5H-dibenzo[a,d]cyclohepten-5-one |

PREPARATION 2.

10,11-Dihydro-5,5,10,10,11,11-hexafluoro-5H-dibenzo[a,d]cycloheptene 10,11-Dihydro-5H-dibenzo[a,d]cycloheptene-10,11-dione, 1.0 g. (0.0045 mole), together with 48 g. of sulfur tetrafluoride, 1 g. of mercury and a trace of hydrogen fluoride, is charged into a stainless steel autoclave and shaken 10 hours at 80°C. After cooling and venting the vessel, the mixture is dissolved in chloroform, separated from mercury, and filtered. Evaporation of solvent from the filtrate under reduced pressure leaves an oily dark blue residue that is triturated with 150 ml. of boiling hexane. The hexane-insoluble material is removed by filtration and evaporation of solvent from the filtrate under reduced pressure leaves the crude product as the residue. Sublimation at 70°C. and 0.1 mm. yields oily off-white solid that is triturated with carbon tetrachloride. The insoluble material is removed by filtration and the filtrate is concentrated and applied to a chromatographic column of 70 g. of silica gel. The product is eluted with carbon tetrachloride, collecting the fractions that show essentially one spot of Rf 0.7 on a silica thin layer plate developed with carbon tetrachloride. Evaporation of the solvent under reduced pressure and sublimation of the residue at 55°-60°C. and 0.1 mm. yields white crystals, m.p. 53°-55°C. to a slightly cloudy melt.

Anal. Calc'd. for $C_{15}H_8F_6$: C, 59.61; H, 2.67; F, 37.72. Found: C, 59.54; H, 3.11; F, 35.80.

PREPARATION 3.

10,11-Dihydro-10,10,11,11-tetrafluoro-5H-dibenzo[a,d]cyclohepten-5-one

A solution of 989 mg. (0.00328 mole) of 10,11-dihydro-5,5,10,10,11,11-hexafluoro-5H-dibenzo[a,d]cycloheptene in 13.2 ml. of glacial acetic acid —3.5 ml. of 6 N hydrochloric acid is held at room temperature for approximately 20 hours, heated in a 65°C. bath for 3 hours, again held at room temperature for about 20 hours, and finally heated in a 65°C. bath for 3 hours. The solution is concentrated under reduced pressure and the residue partitioned between benzene and water. The benzene extract is washed with water, dried over anhydrous sodium sulfate, and evaporated to dryness under reduced pressure. Sublimation of the residue at 80°C. and 0.1 mm. yields the crude product as an oily solid. Purification is effected by column chromatography on silica gel, the product being eluted with carbon tetrachloride. The fractions that show one spot of Rf 0.1 on a silica thin layer plate developed with carbon tetrachloride are combined. Evaporation of the solvent under reduced pressure leaves the white crystalline product, m.p. 76°-78°C.

PREPARATION 4.

10,11-Dihydro-10,10,11,11-tetrafluoro-5H-dibenzo[a,d]cycloheptene 10,11-Dihydro-5H-dibenzo[a,d]cycohepten-10,11-dione, 2,2 g. (0.01 mole), together with 107 g. of sulfur tetrafluoride, 1 g. of mercury, a trace of hydrogen fluoride, and 25 ml. of methylene chloride, is charged into a stainless steel autoclave and shaken 10 hours at 80°C. After cooling and venting the vessel, the mixture is separated from mercury and filtered. Evaporation of solvent from the filtrate under reduced pressure leaves a brown oil as the residue that is triturated with 150 ml. of hexane. The insoluble tar is removed by filtration and evaporation of solvent from the filtrate under reduced pressue leaves the crude product as an oil. Sublimation at 50°-55°C. and 0.05 mm. yields white crystals, m.p. 53.5°-55°C. A sample for analysis from a previous preparation was purified by column chromatography on silica gel, eluting the product with carbon tetrachloride. Evaporation of solvent under reduced pressure and sublimation of the residual solid at 60°-70°C. and 0.8 mm. gave purified product, m.p. 53.5°-56°C.

Anal. Calc'd. for $C_{15}H_{10}F_4$: C, 67.67; H, 3.79; F, 28.55. Found: C, 67.38; H, 3.89; F, 28.56.

PREPARATION 5.

10,11-Dihydro-10,10,11,11-tetrafluoro-5H-dibenzo[a,d]cyclohepten-5-one

A mixture of 1.45 g. (0.00544 mole) of 10,11-dihydro-10,10,11,11-tetrafluoro-5H-dibenzo[a,d]cycloheptene, 0.73 g. (0.0073 mole) of chromium trioxide, 25 ml. of trifluoroacetic acid and 2 ml. of glacial acetic acid is stirred at reflux for 2¼ hours. During this period, almost all of the chromium trioxide dissolves. Solvents are evaporated under reduced pressure and the residue is partitioned between benzene and water. The aqueous layer is separated and re-extracted twice with benzene. The combined benzene extracts are washed thoroughly with water, dried over anhydrous magnesium sulfate, and evaporated to dryness under reduced pressure. The crude product is left as the residual oily solid and is purified by column chromatography on 75 g. of silica gel, eluting the product with 1:1 benzene-carbon tetrachloride. The fractions that show one spot of Rf 0.75 on a silica thin layer plate developed with benzene are combined. Evaporation of the solvent under reduced pressure leaves the white crystalline product, m.p. 70°-75°C.

EXAMPLE 1

10,11-Dihydro-10,10,11,11-tetrafluoro-5H-dibenzo[a,d]cyclohepten-5-ol

A solution of 190 mg. (0.0005 mole) of sodium borohydride in 1 ml. of water is added dropwise to a stirred solution of 830 mg. (0.00296 mole) of 10,11-dihydro-10,10,11,11-tetrafluoro-5H-dibenzo[a,d]cyclohepten-5-one in 10 ml. of isopropyl alcohol. After stirring the mixture for 3 hours at room temperature and 30 minutes at reflux, the isopropyl alcohol is evaporated under reduced pressure. The residue is partitioned between benzene and water and the benzene extract is separated, washed, and dried. Evaporation under reduced pressure leaves the product as the residual pale yellow oil. A sample for analysis is evaporatively distilled at 80°C. and 0.1 mm.

Analysis calc'd. for $C_{15}H_{10}F_4$: C, 63.84; H, 3.57; F, 26.94. Found: C, 63.93; H, 3.34; F, 27.78.

The procedure of the preceding paragraph is repeated using as starting material, instead of 10,11-dihydro-10,10-11,11-tetrafluoro-5H-dibenzo[a,d]cyclohepten-5-one, the products obtained in accordance with the second paragraph of Preparation 1 with resultant production of the following products:

10,11-dihydro-1,10,10,11,11-pentafluoro-5H-dibenzo[a,d]-cyclohepten-5-ol 3-chloro-10,11-dihydro-10,10,11,11-tetrafluoro-5H-dibenzo-[a,d]-cyclohepten-5-ol 10,11-dihydro-3-methyl-10,10,11,11-tetrafluro-5H-dibenzo-[a,d]-cyclohepten-5-ol 3,7-diethyl-10,11-dihydro-10,10,11,11-tetrafluoro-5H-dibenzo[a,d]cyclohepten-5-ol 10,11-dihydro-4-methoxy-10,10,11,11-tetrafluoro-5H-dibenzo-[a,d]cyclohepten-5-ol 10,11-dihydro-3-ethoxy-10,10,11,11-tetrafluoro-5H-dibenzo-[a,d]cyclohepten-5-ol 3,7-diethoxy-10,11-dihydro-10,10,11,11-tetrafluoro-5H-dibenzo[a,d]cyclohepten-5-ol 10,11-dihydro-3-trifluoromethyl-10,10,11,11-tetrafluoro-5H-dibenzo[a,d]cyclohepten-5-ol

10,11-dihydro-3-methylmercapto-10,10,11,11-tetrafluoro-5H-dibenzo[a,d]cyclohepten-5-ol

10,11-dihydro-3-propylmercapto-10,10,11,11-tetrafluoro-5H-dibenzo[a,d]cyclohepten-5-ol 10,11-dihydro-3-ethylsulfonyl-10,10,11,11-tetrafluoro-5H-dibenzo[a,d]cyclohepten-5-ol 3-diethylsulfamoyl-10,11-dihydro-10,10,11,11-tetrafluoro-5H-dibenzo[a,d]cyclohepten-5-ol

EXAMPLE 2

5-Chloro-10,11-dihydro-10,10,11,11-tetrafluoro-5H-dibenzo-[a,d]cycloheptene

A solution of 665 mg. (0.00236 mole) of 10,11-dihydro-10,10,11,11-tetrafluoro-5H-dibenzo[a,d]cyclohepten-5-ol in 5 ml. of dry benzene is stirred, cooled to 10°–15°C. in an ice bath and treated dropwise with 0.2 ml. of thionyl chloride. After allowing the light yellow solution to come to room temperature, it is heated to refluxing for approximately 18 hours and the solution is evaporated to dryness under reduced pressure. The residual solid is flushed with benzene three times to remove the last traces of thionyl chloride and finally dried under reduced pressure at 50°C. for 1 hour, yielding product, m.p. 129°–132°C. Recrystallization from petroleum ether (30°–60°C.) affords a purified sample, m.p. 131.5°–133.5°C.

Anal. Calc'd. for $C_{15}H_9ClF_4$: C, 59.91; H, 3.02; Cl, 11.80. Found: C, 60.25; H, 3.26; Cl, 11.63.

The procedure of the preceding paragraph is repeated using as starting material instead of 10,11-dihydro-10,10,11,11-tetrafluoro-5H-dibenzo[a,d]cyclohepten-5-ol the products obtained in accordance with the second paragraph of Example 1 with resultant production of 5-chloro-10,11-dihydro-1,10,10,11,11-pentafluoro-5H-dibenzo-[a,d]cycloheptene, 3,5-dichloro-10,11-dihydro-10,10,11,11-tetrafluoro-5H-dibenzo[a,d]cycloheptene, 5-chloro-10,11-dihydro-3-methyl-10,10,11,11-tetrafluoro-5H-dibenzo[a,d]cycloheptene, 5-chloro-10,11-dihydro-3,7-dimethyl-10,10,11,11-tetrafluoro-5H-dibenzo[a,d]cycloheptene, 5-chloro-10,11-dihydro-4-methoxy-10,10,11,11-tetrafluoro-5H-dibenzo[a,d]cycloheptene, 5-chloro-10,11-dihydro-3-ethoxy-10,10,11,11-tetrafluoro-5H-dibenzo[a,d]cycloheptene, 5-chloro-3,7-diethoxy-10,11-dihydro-10,10,11,11-tetrafluoro-5H-dibenzo[a,d]cycloheptene, 5-chloro-10,11-dihydro-3-trifluoromethyl-10,10,11,11-tetrafluoro-5H-dibenzo[a,d]cycloheptene, 5-chloro-10,11-dihydro-3-methylmercapto-10,10,11,11-tetrafluoro-5H-dibenzo[a,d]cycloheptene, 5-chloro-10,11-dihydro-4-propylmercapto-10,10,11,11-tetrafluoro-5H-dibenzo[a,d]cycloheptene, 5-chloro-10,11-dihydro-3-ethylsulfonyl-10,10,11,11-tetrafluoro-5H-dibenzo[a,d]cycloheptene, and 5-chloro-3-diethylsulfamoyl-10,11-dihydro-10,10,11,11-tetrafluoro-5H-dibenzo[a,d]cycloheptene.

EXAMPLE 3

Diethyl-10,11-dihydro-10,10,11,11-tetrafluoro-5H-dibenzo[a,d]cycloheptene-5-malonate Diethyl malonate, 90 ml., is stirred, cooled in an ice bath, and treated with 1.51 g. of 55.7% sodium hydride in mineral oil in several portions. The mixture is stirred approximately 5 minutes at room temperature and then treated with 10.03 g. (0.0334 mole) of 5-chloro-10,11-dihydro-10,10,11,11-tetrafluoro-5H-dibenzo[a,d]cycloheptene. Stirring is continued for 16 hours at approximately 40°C., 1 hour at 50°C., 1 hour at 60°C. and 1 hour at 70°C. The excess diethyl malonate is distilled at 70°–75°C. and 0.1 mm. and the residue is triturated with hexane. The insoluble mixture of product and sodium chloride is collected, washed with hexane and petroleum ether, and dried at 80°C. and 0.1 mm. The mixture is triturated with benzene and the insoluble sodium chloride is removed by filtration. Evaporation of the benzene solution under reduced pressure and recrystallization of the residual white solid from absolute ethanol affords purified product, m.p. 144°–146°C.

Anal. Calc'd. for $C_{22}H_{20}F_4O_4$ : C, 62.26; H, 4.75; F, 17.90. Found: C, 62.59; H, 4.52; F, 17.46.

The procedure of the preceding paragraph is repeated using as starting materials, instead of 5-chloro-10,11-dihydro-10,10,11,11-tetrafluoro-5H-dibenzo[a,d]cycloheptene, the products obtained in accordance with the second paragraph of Example 2 with resultant production of Diethyl-10,11-dihydro-1,10,10,11,11-pentafluoro-5H-dibenzo-[a,d]cycloheptene-5-malonate Diethyl-3-chloro-10,11-dihydro-10,10,11,11-tetrafluoro-5H-dibenzo[a,d]cycloheptene-5-malonate Diethyl-10,11-dihydro-3-methyl-10,10,11,11-tetrafluoro-5H-dibenzo[a,d]cycloheptene-5-malonate Diethyl-3,7-diethyl-10,11-dihydro-10,10,11,11-tetrafluoro-5H-dibenzo[a,d]cycloheptene-5-malonate Diethyl-10,11-dihydro-4-methoxy-10,10,11,11-tetrafluoro-5H-dibenzo[a,d]cycloheptene-5-malonate Diethyl-10,11-dihydro-3-ethoxy-10,10,11,11-tetrafluoro-5H-dibenzo[a,d]cycloheptene-5-malonate, Diethyl-3,7-diethoxy-10,11-dihydro-10,10,11,11-tetrafluoro-5H-dibenzo[a,d]cycloheptene-5-malonate Diethyl-10,11-dihydro-3-trifluoromethyl-10,10,11,11-tetrafluoro-5H-dibenzo[a,d]cycloheptene-5-malonate Diethyl-10,11-dihydro-3-methylmercapto-10,10,11,11-tetrafluoro-5H-dibenzo[a,d]cycloheptene-5-malonate Diethyl-10,11-dihydro-4-propylmercapto-10,10,11,11-tetrafluoro-5H-dibenzo[a,d]cycloheptene-5-malonate Diethyl-10,11-dihydro-3-ethylsulfonyl-10,10,11,11-tetrafluoro-5H-dibenzo[a,d]cycloheptene-5-malonate, and Diethyl-3-diethylsulfamoyl-10,11-dihydro-10,10,11,11-tetrafluoro-5H-dibenzo[a,d]cycloheptene-5-malonate.

EXAMPLE 4

10,11-Dihydro-10,10,11,11-tetrafluoro-5H-dibenzo[a,d]-cycloheptene-5-acetic acid A solution of 0.01525 mole of diethyl 10,11-dihydro-10,10,11,11-tetrafluoro-5H-dibenzo[a,d]cycloheptene-5-malonate in 250 ml. of methanol and 30 ml. of 5% aqueous sodium hydroxide is heated to refluxing for 2 hours. Evaporation of the solution under reduced pressure leaves an oil that is partitioned between 5% aqueous sodium hydroxide and benzene. The aqueous alkaline layer is separated, cooled in ice, and acidified with dilute hydrochloric acid. The oily precipitate is extracted into benzene. After concentration of the washed and dried benzene solution to a small volume, the white solid product crystallizes and is collected; m.p. 183°–185°C. Sublimation at 115°C. and 0.05 mm. gives a purified sample, m.p. 179°–186°C.

Anal. Calc'd. for $C_{17}H_{12}F_4O_2$: C, 62.96; H, 3.73; F, 23.44. Found: C, 63.00; H, 3.91; F, 23.31.

The procedure of the preceding paragraph is repeated using as starting materials, instead of diethyl-10,11-dihydro -10,10,11,11-tetrafluoro-5H-dibenzo[a,d]cycloheptene-5-malonate, the products obtained in accordance with the second paragraph of Example 3 with resultant production of 10,11-dihydro-1,10,10,11,11-pentafluoro-5H-dibenzo[a,d]-cycloheptene-5-acetic acid, 3-chloro-10,11-dihydro-10,10,11,11-tetrafluoro-5H-dibenzo-[a,d]cycloheptene-5-acetic acid, 10,11-dihydro-3-methyl-10,10,11,11-tetrafluoro-5H-dibenzo-[a,d]cycloheptene-5-acetic acid, 3,7-diethyl-10,11-dihydro-10,10,11,11-tetrafluoro-5H-dibenzo[a,d]cycloheptene-5-acetic acid, 10,11-dihydro-4-methoxy-10,10,11,11-tetrafluoro-5H-dibenzo-[a,d]cycloheptene-5-acetic acid, 10,11-dihydro-3-ethoxy-10,10,11,11-tetrafluoro-5H-dibenzo[a,d]-cycloheptene-5-acetic acid, 3,7-diethoxy-10,11-dihydro-10,10,11,11-tetrafluoro-5H-dibenzo[a,d]cycloheptene-5-acetic acid, 10,11-dihydro-3-trifluoromethyl-10,10,11,11-tetrafluoro-5H-dibenzo[a,d]cycloheptene-5-acetic acid, 10,11-dihydro-3-methylmercapto-10,10,11,11-tetrafluoro-5H-dibenzo[a,d]cycloheptene-5-acetic acid, 10,11-dihydro-4-propylmercapto-10,10,11,11-tetrafluoro-5H-dibenzo[a,d]cycloheptene-5-acetic acid, 10,11-dihydro-3-ethylsulfonyl-10,10,11,11-tetrafluoro-5H-dibenzo[a,d]cycloheptene-5-acetic acid, and 3-diethylsulfamoyl-10,11-dihydro-10,10,11,11-tetrafluoro-5H-dibenzo[a,d]cycloheptene-5-acetic acid.

EXAMPLE 5

10,11-Dihydro-N-methoxycarbonyl-10,10,11,11-tetrafluoro-5H-dibenzo[a,d]cycloheptene-5-methylamine 10,11-Dihydro-10,10,11,11-tetrafluoro-5H-dibenzo-[a,d]cycloheptene-5-acetic acid, 0.663 g. (0.00205 mole), is dissolved in 0.4 ml. of water − 2.5 ml. of acetone. The solution is stirred, cooled in an ice-salt bath, and treated with a solution of 0.24 g. (0.00236 mole) of triethylamine in 2 ml. of acetone. A solution of 0.28 g. (0.0026 mole) of ethyl chloroformate in 1.2 ml. of acetone is added dropwise and stirring is continued at 0°C. for 1¼ hours. A solution of 0.2 g. (0.00308 mole) of sodium azide in 0.6 ml. of water then is added dropwise. After 1 hour of stirring in the cold, the mixture is poured into 80 ml. of water and the oily product extracted into toluene. The washed and dried toluene extract is heated at 90°C. for 20 minutes and then evaporated to dryness under reduced pressure. The residual oil is dissolved in 10 ml. of absolute methanol and after heating the solution to refluxing for 15 minutes, the solvent is evaporated under reduced pressure. Recrystallization of the residual solid from hexane yields the white crystalline product, m.p. 137°–139.5°C.

The procedure of the preceding paragraph is repeated using as starting materials, instead of 10,11-dihydro-10,10,11,11-tetrafluoro-5H-dibenzo[a,d]-cycloheptene-5-acetic acid, the products obtained in accordance with the second paragraph of Example 4 with resultant production of 10,11-dihydro-N-methoxycarbonyl-1,10,10,11,11-pentafluoro-5H-dibenzo[a,d]cycloheptene-5-methylamine, 3-chloro-10,11-dihydro-N-methoxycarbonyl-10,10,11,11-tetrafluoro-5H-dibenzo[a,d]cycloheptene-5-methylamine, 10,11-dihydro-3-methyl-N-methoxycarbonyl-10,10,11,11-tetrafluoro-5H-dibenzo[a,d]cycloheptene-5-methylamine, 3,7-diethyl-10,11-dihydro-N-methoxycarbonyl-10,10,11,11-tetrafluoro-5H-dibenzo[a,d]cycloheptene-5-methylamine, 10,11-dihydro-4-methoxy-N-methoxycarbonyl-10,10,11,11-tetrafluoro-5H-dibenzo[a,d]cycloheptene-5-methylamine, 10,11-dihydro-3-ethoxy-N-methoxycarbonyl-10,10,11,11-tetrafluoro-5H-dibenzo[a,d]cycloheptene-5-methylamine, 3-diethoxy-10,11-dihydro-N-methoxycarbonyl-10,10,11,11-tetrafluoro-5H-dibenzo[a,d]cycloheptene-5-methylamine, 10,11-dihydro-3-trifluoromethyl-N-methoxycarbonyl-10,10,11,11-tetrafluoro-5H-dibenzo[8 a,d]cycloheptene-5-methylamine, 10,11-dihydro-3-methylmercapto-N-methoxycarbonyl-10,10,11,11-tetrafluoro-5H-dibenzo[8 a,d]cycloheptene-5-methylamine, 10,11-dihydro-4-propylmercapto-N-methoxycarbonyl-10,10,11,11-tetrafluoro-5H-dibenzo[a,d]cycloheptene-5-methylamine, 10,11-dihydro-3-ethylsulfonyl-N-methoxycarbonyl-10,10,11,11-tetrafluoro-5H-dibenzo[a,d]cycloheptene-5-methylamine, and 3-diethylsulfamoyl-10,11-dihydro-N-methoxycarbonyl-10,10,11,11-tetrafluoro-5H-dibenzo[a,d]cycloheptene-5-methylamine.

EXAMPLE 6

10,11-Dihydro-N-methyl-10,10,11,11-tetrafluoro-5H-dibenzo-[a,d]cycloheptene-5-methylamine Lithium aluminum hydride, 0.119 g. (0.00313 mole) is weighed under nitrogen, transferred to a dry, nitrogen-flushed reaction flask, and suspended in 5 ml. of absolute ether. A solution of 0.416 g. (0.00313 mole) of anhydrous aluminum chloride in 10 ml. of absolute ether is added dropwise. After stirring the mixture for several minutes, a solution of 0.3 g. (0.00085 mole) of 10,11-dihydro-N-methoxycarbonyl-10,10,11,11-tetrafluoro-5H-dibenzo[a,d]-cycloheptene-5-methylamine in 10 ml. of absolute ether is added dropwise. Stirring is continued overnight in a nitrogen atmosphere. The mixture is cooled in an ice bath and hydrolyzed by the dropwise addition of 4 ml. of water. The ethereal solution is decanted and the gelatinous precipitate, after washing twice with ether, is treated with 8 ml. of 40% aqueous sodium hydroxide and 40 ml. of water. The oily base is extracted into benzene. Evaporation of the washed and dried benzene extract under reduced pressure leaves the product as the residual oil. The base is converted to the hydrochloride salt by treating a solution in absolute ethanol with a slight excess of ethanolic hydrogen chloride. After dilution with absolute ether, the precipitated hydrochloride is collected; m.p. 249.5°–251°C. Recrystallization from isopropyl alcohol-absolute ether gives a purified sample, m.p. 252°–253°C.

Anal. Calc.'d. for $C_{17}H_{15}F_4N.HCl$: C, 59.05; H, 4.67; N, 4.05. Found: C, 58.92; H, 4.79; N, 4.07.

The procedure of the preceding paragraph is repeated using as the starting materials, instead of 10,11-dihydro-N-methoxycarbonyl-10,10,11,11-tetrafluoro-5H-dibenzo[a,d]-cycloheptene-5-methylamine, the products obtained in accordance with the second paragraph of Example 5 with the resultant production of 10,11-dihydro-N-methyl-1,10,10,11,11-pentafluoro-5H-dibenzo-[a,d]cycloheptene-5-methylamine, 3-chloro-10,11-dihydro-N-methyl-10,10,11,11-tetrafluoro-5H-dibenzo[a,d]cycloheptene-5-methylamine, 10,11-dihydro-3-methyl-N-methyl-10,10,11,11-tetrafluoro-5H-dibenzo[a,d]cycloheptene-5-methylamine, 3,7-diethyl-10,11-dihydro-N-methyl-10,10,11,11-tetrafluoro-5H-dibenzo[a,d]cycloheptene-5-methylamine, 10,11-dihydro-4-methoxy-N-methyl-10,10,11,11-tetrafluoro-5H-dibenzo[a,d]cycloheptene-5-methylamine, 10,11-dihydro-3-ethoxy-N-methyl-10,10,11,11-tetrafluoro-5H-dibenzo[a,d]cycloheptene-5-methylamine, 3,7-diethoxy-10,11-dihydro-N-methyl-10,10,11,11-tetrafluoro-5H-dibenzo[a,d]cycloheptene-5-methylamine, 10,11-dihydro-3-trifluoromethyl-N-methyl-10,10,11,11-tetrafluoro-5H-dibenzo[a,d]cycloheptene-5-methylamine, 10,11-dihydro-3-methylmercapto-N-methyl-10,10,11,11-tetrafluoro-5H-dibenzo[a,d]cycloheptene-5-methylamine, 10,11-dihydro-4-propylmercapto-N-methyl-10,10,11,11-tetrafluoro-5H-dibenzo[a,d]cycloheptene-5-methylamine, 10,11-dihydro-3-ethylsulfonyl-N-methyl-10,10,11,11-tetrafluoro-5H-dibenzo[a,d]cycloheptene-5-methylamine, and 3-diethylsulfamoyl-10,11-dihydro-N-methyl-10,10,11,11-tetrafluoro-5H-dibenzo[a,d]cycloheptene-5-methylamine.

EXAMPLE 7

10,11-Dihydro-10,10,11,11-tetrafluoro-5H-dibenzo-[a,d]cycloheptene-5-methylamine 10,11-Dihydro-N-methoxycarbonyl-10,10,11,11-tetrafluoro-5H-dibenzo[a,d]cycloheptene-5-methylamine, 0.5 g. (0.001417 mole), together with 5 ml. of glacial acetic acid, 2.5 ml. of water, and 2.5 ml. of concentrated hydrochloric acid, is stirred at reflux for 20 hours. Evaporation of the solution under reduced pressure and recrystallization of the residual solid from absolute methanol-absolute ether yields the hydrochloride salt of the product, m.p. 250°–255°C. Repeated crystallizations from isopropyl alcohol - absolute ether afford the analytical sample, m.p. 268°–271°C.

Anal. Calc'd. for $C_{16}H_{13}F_4N.HCl$: C, 57.92; H, 4.25; Cl, 10.69. Found: C, 57.84; H, 4.32; Cl, 10.73.

The procedure of the preceding paragraph is repeated using as the starting materials, instead of 10,11-dihydro-N-methoxycarbonyl-10,10,11,11-tetrafluoro-5H-dibenzo[a,d]-cycloheptene-5-methylamine, the products obtained in accordance with the second paragraph of Example 6 with the resultant production of 10,11-dihydro-1,10,10,11,11-pentafluoro-5H-dibenzo[a,d]-cycloheptene-5-methylamine, 3-chloro-10,11-dihydro-10,10,11,11-tetrafluoro-5H-dibenzo-[a,d]cycloheptene-5-methylamine, 10,11-dihydro-3-methyl-10,10,11,11-tetrafluoro-5H-dibenzo-[a,d]cycloheptene-5-methylamine, 3,7-diethyl-10,11-dihydro-10,10,11,11-tetrafluoro-5H-dibenzo[a,d]cycloheptene-5-methylamine, 10,11-dihydro-4-methoxy-10,10,11,11-tetrafluoro-5H-dibenzo[a,d]cycloheptene-5-methylamine, 10,11-dihydro-3-ethoxy-10,10,11,11-tetrafluoro-5H-dibenzo[a,d]cycloheptene-5-methylamine, 3,7-diethoxy-10,11-dihydro-10,10,11,11-tetrafluoro-5H-dibenzo[a,d]cycloheptene-5-methylamine, 10,11-dihydro-3-trifluoromethyl-10,10,11,11-tetrafluoro-5H-dibenzo[a,d]cycloheptene-5-methylamine, 10,11-dihydro-3-methylmercapto-10,10,11,11-tetrafluoro-5H-dibenzo[a,d]cycloheptene-5-methylamine, 10,11-dihydro-3-ethylsulfonyl-10,10,11,11-tetrafluoro-5H-dibenzo[a,d]cycloheptene-5-methylamine, 3-ethylsulfamoyl-10,11-dihydro-10,10,11,11-tetrafluoro-5H-dibenzo[a,d]cycloheptene-5-methylamine, and 10,11-dihydro-4-propylmercapto-10,10,11,11-tetrafluoro-5H-dibenzo[a,d]cycloheptene-5-methylamine.

EXAMPLE 8

METHOD OF TESTING FOR ANTIARRHYTHMIC ACTIVITY - PREVENTION OR MODIFICATION OF VENTRICULAR ARRHYTHMIA

Beagle dogs of either sex and weighing from 6 to 10 kg. are anesthetized by the administration of vinbarbital employing a dose of 50 mg./kg. of body weight and the mean arterial pressure and the electrocardiogram (Lead II) are recorded. The animals are artificially respired and the thorax opened at the fourth or fifth interspace. The pericardium is opened and a portion of the anterior descending coronary artery just distal to the origin is freed from the surrounding tissue. Mecamylamine is administered to slow the heart rate and 10 minutes later the compound to be tested for antiarrhythmic effect is administered intravenously. Ten minutes after administration of the test compound 0.0035 ml./kg. of tetrafluorohexachlorobutane (TFHCB), a sclerosing agent which produces myocardial infarction and arrhythmia in dogs (Ascanio et al., J. Am. Physiol. 209: 1081–1099 (1965) ) is injected into the coronary artery. In control animals, this dose of TFHCB produces a ventricular arrhythmia in 100% of the animals tested and death in 33% of the animals tested as a result of ventricular fibrillation.

Following injection of the sclerosing agent, an electrocardiogram is recorded at two-miute intervals for one hour and the average number of electrical (ECG) complexes per minute and the percent normal complexes calculated. The data obtained with different doses of the test compounds is plotted and the dose estimated to protect the animals is estimated graphically ($ED_{80}$ mg./kg.). This figure indicates that 80% of all the electrical (ECG) complexes are normal.

The compound, 10,11-dihydro-10,10,11,11-tetrafluoro-5H-dibenzo[a,d]cycloheptene-5-methylamine, is active as an antiarrhythmic agent.

EXAMPLE 9

METHOD OF TESTING FOR ANTIARRHYTHMIC ACTIVITY - TREATMENT OF EXISTING ARRHYTHMIA

The compounds to be tested for antiarrhythmic effect are tested in animals with an arrhythmia due to ligation of a branch of the coronary artery. The technique used to produce the arrhythmia is described by Harris (Circ. 1:1318–1328, 1950). The test compounds are examined for their effect on total electrical rate (ECG) and ventricular ectopic rhythms.

The test animals are 6 to 10 kg. unanesthetized beagle dogs in which the anterior descending coronary artery has been ligated one or two days prior to the test. Lead II of the ECG is recorded, the total electrical rate per minute is computed and the percent normal complexes calculated at 15-minute intervals before and after administration of the test compound. The measurements are made over a total of two hours for the 60 minutes during and the 60 minutes following administration of the test drug. To evaluate the effectiveness of the compound, data from four or more observations are averaged and plotted graphically. The area formed by the curves is measured with a planimeter. The degree of effectiveness of the test compounds is related to the size of the area under the curve. The test compound is compared to the known antiarrhythmic agent, quinidine sulfate, in this test.

The compound 10,11-dihydro-10,10,11,11-tetrafluoro-5H-dibenzo[a,d]cycloheptene-5-methylamine, is active in this test as an antiarrhythmic agent.

What is claimed is:

1. A compound of the formula

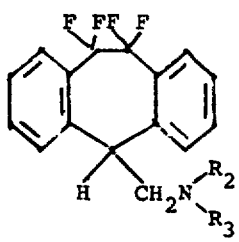

wherein $R_2$ and $R_3$ are similar or dissimilar and are either hydrogen or loweralkyl, or a derivative thereof in which one or two of the hydrogens at the 1-, 2-, 3-, 4-, 6-,7-, 8- or 9-positions is replaced with a substituent selected from hydrogen, halogen, loweralkyl, loweralkoxy, perfluoroloweralkyl, loweralkylmercapto and loweralkylsulfonyl.

2. A compound of the formula

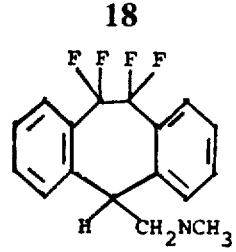

in which one or two of the hydrogens at the 1-,2-, 3-, 4-, 6-, 7-, 8-, 9-positions is replaced with a substituent selected from hydrogen, halogen, loweralkyl, loweralkoxy, perfluoroloweralkyl, loweralkylmercapto and loweralkylsulfonyl.

3. 10,11-Dihydro-N-methyl-10,10,11,11-tetrafluoro-5H-dibenzo[a,d]cycloheptene-5-methylamine.

4. A compound of the formula

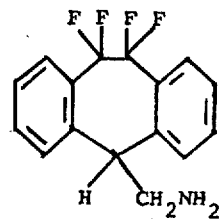

in which one or two of the hydrogens at the 1-, 2-, 3-, 4-, 6-, 7-, 8- or 9-positions is replaced with a substituent selected from hydrogen, halogen, loweralkyl, perfluoroloweralkyl, loweralkoxy, loweralkylmercapto or loweralkylsulfonyl.

5. 10,11-Dihydro-10,10,11,11-tetrafluoro-5H-dibenzo[a,d]cycloheptene-5-methylamine.

6. A compound of the formula

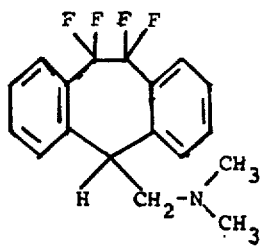

in which one or two of the hydrogens at the 1-, 2-, 3-, 4-, 6-, 7-, 8or 9-positions is replaced with a substituent selected from hydrogen, halogen, loweralkyl, loweralkoxy, perfluoroloweralkyl, loweralkylmercapto or loweralkylsulfonyl.

7. 10,11-Dihydro-10,10,11,11-tetrafluoro-N,N-dimethyl-5H-dibenzo[a,d]cycloheptene-5-methylamine.

* * * * *